United States Patent
Tanimura et al.

(10) Patent No.: US 10,350,194 B2
(45) Date of Patent: Jul. 16, 2019

(54) PHARMACEUTICAL COMPOSITION CONTAINING AN ARYLALKYLAMINE COMPOUND

(71) Applicant: KYOWA HAKKO KIRIN CO., LTD., Chiyoda-ku (JP)

(72) Inventors: Shinji Tanimura, Chiyoda-ku (JP); Hiroko Yoshii, Chiyoda-ku (JP); Kenji Iwata, Chiyoda-ku (JP); Naoto Izawa, Chiyoda-ku (JP); Motohiro Ota, Chiyoda-ku (JP)

(73) Assignee: KYOWA HAKKO KIRIN CO., LTD., Chiyoda-ku (JP)

( * ) Notice: Subject to any disclaimer, the term of this patent is extended or adjusted under 35 U.S.C. 154(b) by 0 days.

(21) Appl. No.: 15/766,426

(22) PCT Filed: Oct. 7, 2016

(86) PCT No.: PCT/JP2016/080013
§ 371 (c)(1),
(2) Date: Apr. 6, 2018

(87) PCT Pub. No.: WO2017/061621
PCT Pub. Date: Apr. 13, 2017

(65) Prior Publication Data
US 2018/0296526 A1   Oct. 18, 2018

(30) Foreign Application Priority Data

Oct. 7, 2015   (JP) ................................. 2015-199694
Oct. 6, 2016   (JP) ................................. 2016-197725

(51) Int. Cl.
*A61K 31/402*   (2006.01)
*A61K 9/20*     (2006.01)
*A61K 9/28*     (2006.01)

(52) U.S. Cl.
CPC .......... *A61K 31/402* (2013.01); *A61K 9/2009* (2013.01); *A61K 9/2018* (2013.01); *A61K 9/2027* (2013.01); *A61K 9/2031* (2013.01); *A61K 9/2054* (2013.01); *A61K 9/2059* (2013.01); *A61K 9/2068* (2013.01); *A61K 9/2853* (2013.01); *A61K 9/2866* (2013.01); *A61K 9/2886* (2013.01)

(58) Field of Classification Search
CPC ........ A61K 31/402; A61K 9/14; A61K 47/02; A61K 47/10; A61K 47/26; A61K 47/32; A61K 47/36; A61K 47/38; A61K 47/42; A61K 47/46; A61K 9/16; A61K 9/20; A61K 9/2009; A61K 9/2018; A61K 9/2027; A61K 9/2054; A61K 9/2059; A61K 9/2068; A61K 9/2853; A61K 9/48
See application file for complete search history.

(56) References Cited

U.S. PATENT DOCUMENTS

| | | | |
|---|---|---|---|
| 8,362,274 B2 * | 1/2013 | Miyazaki | C07D 205/04 548/400 |
| 2005/0129760 A1 | 6/2005 | Muskulus et al. | |
| 2006/0134192 A1 | 6/2006 | Uchida et al. | |
| 2007/0082047 A1 | 4/2007 | Sugaya et al. | |
| 2007/0110803 A1 | 5/2007 | Konieczna et al. | |
| 2007/0185211 A1 * | 8/2007 | Wizel | A61K 31/137 514/649 |
| 2007/0225296 A1 | 9/2007 | Miyazaki et al. | |
| 2008/0318970 A1 * | 12/2008 | Giwercman | A61K 31/352 514/252.13 |
| 2009/0285891 A1 * | 11/2009 | Jung | A61K 9/5078 424/484 |
| 2011/0014243 A1 | 1/2011 | Andersson et al. | |
| 2011/0305758 A1 | 12/2011 | Matono et al. | |
| 2011/0318417 A1 * | 12/2011 | Sebastian | C07C 211/30 424/489 |
| 2016/0200679 A1 | 7/2016 | Miyazaki et al. | |

FOREIGN PATENT DOCUMENTS

| | | |
|---|---|---|
| JP | 55-47615 A | 4/1980 |
| JP | 3-184917 A | 8/1991 |
| JP | 2001-233766 A | 8/2001 |
| JP | 2003-104887 A | 4/2003 |
| JP | 2004-346066 A | 12/2004 |
| JP | 2005-154431 A | 6/2005 |
| JP | 2005-263790 A | 9/2005 |
| JP | 2005-536527 A | 12/2005 |
| JP | 2011-506373 A | 3/2011 |
| JP | 4880457 B2 | 12/2011 |
| JP | 2012-56948 A | 3/2012 |
| JP | 2013-514303 A | 4/2013 |
| WO | WO 2005/030219 A1 | 4/2005 |
| WO | WO 2005/115975 A1 | 12/2005 |
| WO | WO 2010/087462 A1 | 8/2010 |

(Continued)

OTHER PUBLICATIONS

WO2011082980 translation (Year: 2011).*
International Search Report dated Dec. 20, 2016 in PCT/JP2016/080013 (with English translation), 11 pages.
International Preliminary Report on Patentability and Written Opinion of the International Searching Authority dated Apr. 10, 2018 in PCT/JP2016/080013 filed Oct. 7, 2016 (with English translation), 23 pages.
"Shin Yakuzaigaku Soron" 3rd Edition, Nanzando Co., Ltd., Apr. 10, 1987, pp. 369, 370, 414-416 and a cover page (with English translation).
"Yakuzaigaku Manual" 1st edition, Nanzando Co., Ltd., Mar. 20, 1989, p. 122 and a cover page (with English translation).

(Continued)

*Primary Examiner* — Jafar F Parsa
*Assistant Examiner* — Blaine G Doletski
(74) *Attorney, Agent, or Firm* — Oblon, McClelland, Maier & Neustadt, L.L.P.

(57) ABSTRACT

The present invention provides a pharmaceutical composition and the like comprising (4-{(3S)-3-[(1R)-1-(naphthalen-1-yl)ethylamino]pyrrolidin-1-yl}phenyl)acetic acid (Compound A) or a pharmacologically acceptable salt thereof and a diluent.

20 Claims, No Drawings

(56) References Cited

FOREIGN PATENT DOCUMENTS

| WO | WO 2011/082980 A2 | | 7/2011 |
| WO | WO2011082980 | * | 7/2011 |
| WO | WO 2015/034031 A1 | | 3/2015 |

OTHER PUBLICATIONS

Edward M. Brown, et al., "Cloning and charaterization of an Extracellular $Ca^{2+}$-Sensing Receptor from Bovine Parathyroid" Letters to Nature, vol. 366, Dec. 9, 1993, pp. 575-580.

Edward F. Nemeth, et al., "Calcimimetics with Potent and Selective Activity on the Parathyroid Calcium Receptor" Proc. Natl. Acad. Sci. vol. 95, Mar. 1998, pp. 4040-4045.

Edward M. Brown, "Extracellular Ca2+ -Sensing Receptor: Central Mediator of Systemic Calcium Homeostasis" Annu. Rev. Nutr., vol. 20, 2000, pp. 507-533.

Naibedya Chattopadhyay, "Biochemistry, Physiology and Pathophysiology of the Extracellular Calcium-Sensing Receptor" The International Journal of Biochemistry & Cell Biology, vol. 32, 2000, pp. 789-804.

Jack W. Coburn, et al., "Calcimimetic Agents and the Calcium-Sensing Receptor" Curr. Opin. Nephrol. Hypertens., vol. 9, 2000, pp. 123-132.

New General Theory of Pharmaceutics (Revised 3rd Edition), K.K. Nanzando, Apr. 10, 1987, pp. 143-147 and a cover page (with English translation).

Volker Bühier, "Kollicoat Grades, Funtional Polymers for the Pharmaceutical Industry" BASF, Jan. 2007, 6 Pages.

Praveen Kumar Gaur, et al., "Film Coating Technology: Past, Present and Future" Journal of Pharmaceutical Sciences and Pharmacology, vol. 1, No. 1, 2014, pp. 57-67.

* cited by examiner

PHARMACEUTICAL COMPOSITION CONTAINING AN ARYLALKYLAMINE COMPOUND

CROSS-REFERENCE TO RELATED APPLICATION

The present patent application claims priority to Japanese Patent Application No. 2015-199694 filed on Oct. 7, 2015 and Japanese Patent Application No. 2016-197725 filed on Oct. 6, 2016, the entire disclosure of which is incorporated herein by reference.

FIELD OF THE INVENTION

The present invention relates to a pharmaceutical composition and the like comprising an arylalkylamine compound that has an activating action affecting a calcium-sensing receptor (CaSR) and is useful as a medicine particularly for preventing or treating hyperparathyroidism and the like.

BACKGROUND ART

Parathyroid hormone (PTH) is a hormone having a physiological function which induces the absorption of bones to increase blood calcium (Ca) levels, and the hormone plays a role in maintaining the homeostasis of blood Ca levels. When hypersecretion of PTH chronically persists, the concentration of blood Ca increases by the continuous elution of Ca from bones, and as a result metabolic disorders are developed. Therefore, the secretion and synthesis of PTH are strictly controlled by signal transduction mediated by a Ca sensing receptor (CaSR) that detects extracellular calcium ion ($Ca^{2+}$) concentration. Also, it is reported that a compound with an activating action affecting CaSR is expected to exert an enhancing effect of antihyperparathyroidism by lowering the concentration of blood PTH (refer to patent document 1 and non-patent documents 1 to 5).

Meanwhile, patent document 1 discloses (4-{(3S)-3-[(1R)-1-(naphthalen-1-yl)ethylamino]pyrrolidin-1-yl}phenyl)acetic acid (hereinafter referred to as "Compound A") represented by the following formula as an arylalkylamine compound having an activating or antagonistic action affecting CaSR.

[Chemical formula 1]

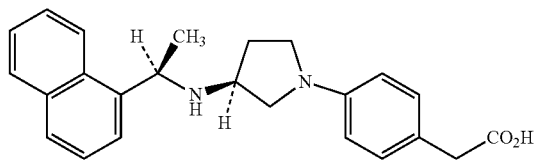

Compound A

However, patent document 1 does not disclose any physical and chemical properties such as stability of Compound A against light or heat (temperature) and does not disclose any pharmaceutical composition comprising Compound A which can be used as a pharmaceutical product either. Meanwhile, patent document 5 discloses a result of a stability test of a crystal form of Compound A.

Also, patent document 2 discloses that the stability of an active pharmaceutical ingredient (topiramate) is improved through the decrease of the production of sulfate ions under the condition of a temperature/humidity environment by blending calcium carbonate with inner core granules of coated granules. Patent document 3 describes the photostability of a diarylvinylene compound contained in the inner core tablet that is improved by coating with an opaque film through the presence of an inorganic substance and/or a coloring agent in a coating film in a tablet. Patent document 4 describes the reduction of the production of impurities under the condition of temperature/humidity environment by blending crystalline cellulose in a tablet to improve the stability of levothyroxine as an active pharmaceutical ingredient. However, as in patent document 1, none of patent documents 2 to 4 discloses a pharmaceutical composition comprising Compound A that can be used as a pharmaceutical product.

PRIOR ART DOCUMENTS

Patent Documents

[Patent Document 1] WO 2005/115975
[Patent Document 2] Japanese Patent Laid-Open Publication No. 2012-056948
[Patent Document 3] WO 2005/030219
[Patent Document 4] Japanese Patent No. 4880457
[Patent Document 5] WO 2015/034031

Non-Patent Documents

[Non-patent Document 1] Nature, 366: p. 575-580, 1993.
[Non-patent Document 2] Proc. Natl. Acad. Sci. USA, 95: p. 4040-4045, 1998.
[Non-patent Document 3] Annu. Rev. Nutr., 20: p. 507-533, 2000.
[Non-patent Document 4] The International Journal of Biochemistry & Cell Biology, 32: p. 789-804, 2000.
[Non-patent Document 5] Curr. Opin. Nephrol. Hypertens., 9, p. 123-132, 2000.

SUMMARY OF THE INVENTION

An object of the present invention is to provide a stable pharmaceutical composition and the like comprising an arylalkylamine compound that is useful for preventing or treating hyperparathyroidism and the like, and can be acceptable as a pharmaceutical product.

The present invention relates to the following clauses (1) to (39).

(1) A pharmaceutical composition comprising (4-{(3S)-3-[(1R)-1-(naphthalen-1-yl)ethylamino]pyrrolidin-1-yl}phenyl)acetic acid (Compound A) or a pharmacologically acceptable salt thereof and a diluent.

(2) The pharmaceutical composition according to the clause (1), wherein the diluent is one or more kinds of material(s) selected from sugar, sugar alcohol, cellulose derivative, starch derivative and inorganic salt.

(3) The pharmaceutical composition according to the clause (1) or (2), wherein the diluent is one or more kinds of material(s) selected from lactose, white (refined) sugar, maltose, sucrose, mannitol, sorbitol, erythritol, maltitol, xylitol, glucose, crystalline cellulose, corn starch, potato starch, calcium monohydrogen phosphate, calcium dihydrogen phosphate, sodium dihydrogen phosphate and calcium phosphate.

(4) The pharmaceutical composition according to any one of the clauses (1) to (3), wherein the diluent is contained in an amount of from 0.1 parts by weight to 99.9 parts by weight per 100 parts by weight of the pharmaceutical composition.

(5) The pharmaceutical composition according to any one of the clauses (1) to (4), further comprising one or more additive(s) selected from binder, basic additive, disintegrant, lubricant, coloring agent and polishing agent.

(6) The pharmaceutical composition according to the clause (5), wherein the binder is one or more kinds of material(s) selected from hydroxypropylcellulose, hydroxypropylmethylcellulose, methylcellulose, carboxymethylcellulose, carboxymethylethylcellulose, hydroxypropyl starch, hydroxyethylcellulose, hydroxypropylmethylcellulose acetate succinate, hydroxypropylmethylcellulose phthalate, carboxyvinyl polymer, polyvinylpyrrolidone, polyvinyl alcohol, methacrylate copolymer, macrogol, starch, gelatin, dextrin, pullulan, agar and gum Arabic.

(7) The pharmaceutical composition according to the clause (5), wherein the basic additive is one or more kinds of material(s) selected from basic oxide, basic hydroxide, carbonate, hydrogencarbonate, silicate and salt of metasilicate aluminate.

(8) The pharmaceutical composition according to the clause (7), wherein the basic additive is one or more kinds of material(s) selected from magnesium oxide, magnesium hydroxide, aluminum hydroxide, sodium carbonate, potassium carbonate, magnesium carbonate, calcium carbonate, sodium hydrogencarbonate, calcium silicate and magnesium aluminometasilicate.

(9) The pharmaceutical composition according to the clause (5), wherein the disintegrant is one or more kinds of material(s) selected from croscarmellose sodium, crospovidone, sodium carboxymethyl starch, low-substituted hydroxypropylcellulose, carboxymethylcellulose, carboxymethylcellulose calcium, partially pregelatinized starch and starch.

(10) The pharmaceutical composition according to the clause (5), wherein the lubricant is one or more kinds of material(s) selected from magnesium stearate, calcium stearate, talc, glyceryl monostearate, light anhydrous silicic acid, sodium stearyl fumarate and sucrose fatty acid esters.

(11) The pharmaceutical composition according to the clause (5), wherein the coloring agent is one or more kinds of material(s) selected from yellow ferric oxide, titanium oxide, talc, ferric oxide, black iron oxide, copper chlorophyll, sodium copper chlorophylline, carbon black, medicinal charcoal, food dye, licorice extract, green tea powder, riboflavin, riboflavin butyrate, riboflavin sodium phosphate, and octyldodecyl myristate.

(12) The pharmaceutical composition according to the clause (5), wherein the polishing agent is one or more kinds of material(s) selected from carnauba wax, shellac, beeswax, hardened oil and magnesium stearate.

(13) The pharmaceutical composition according to any one of the clauses (1) to (12), wherein the additive is contained in an amount of from 0.1 parts by weight to 99.9 parts by weight per 100 parts by weight of the pharmaceutical composition.

(14) The pharmaceutical composition according to any one of the clauses (1) to (13), wherein the pharmaceutical composition has a coating film.

(15) The pharmaceutical composition according to the clause (14), wherein the coating film comprises one or more kinds of coating agent(s) selected from a water-soluble polymer, lactose, white (refined) sugar, titanium oxide and talc.

(16) The pharmaceutical composition according to the clause (15), wherein the water-soluble polymer is one or more kinds of polymer(s) selected from polyvinyl alcohol-polyethylene glycol graft copolymer, polyvinylpyrrolidone, hypromellose, hydroxypropylcellulose, polyvinyl alcohol, polyvinyl alcohol-acrylic acid-methyl methacrylate copolymer and polyethylene glycol.

(17) The pharmaceutical composition according to any one of the clauses (14) to (16), wherein the coating agent is contained in an amount of from 0.1 parts by weight to 100 parts by weight per 100 parts by weight of the coating film.

(18) The pharmaceutical composition according to any one of the clauses (14) to (17), comprising the first coating film comprising a polyvinyl alcohol-polyethylene glycol graft copolymer and the second coating film comprising one or more coating agent(s) selected from a water-soluble polymer, lactose, white (refined) sugar, titanium oxide and talc.

(19) The pharmaceutical composition according to the clause (18), wherein the second coating film comprises one or more coating agent(s) selected from a water-soluble polymer, lactose and titanium oxide.

(20) The pharmaceutical composition according to the clause (19), wherein the second coating film comprises a coloring agent.

(21) A pharmaceutical composition comprising:
an amount of from 0.5 to 5.0 parts by weight of (4-{(3S)-3-[(1R)-1-(naphthalen-1-yl)ethylamino]pyrrolidin-1-yl}phenyl)acetic acid (Compound A) or a pharmacologically acceptable salt thereof,
from 50.0 to 90.0 parts by weight of a diluent,
from 1.0 to 5.0 parts by weight of a binder,
from 0.5 to 5.0 parts by weight of a basic additive,
from 2.0 to 10.0 parts by weight of a disintegrant,
from 0.5 to 3.0 parts by weight of a lubricant,
from 3.0 to 10.0 parts by weight of a coating agent, and
from 0.1 to 1.0 parts by weight of a coloring agent,
per 100 parts by weight of the pharmaceutical composition.

(22) A pharmaceutical composition comprising:
an amount of from 0.5 to 2.0 parts by weight of (4-{(3S)-3-[(1R)-1-(naphthalen-1-yl)ethylamino]pyrrolidin-1-yl}phenyl)acetic acid (Compound A) or a pharmacologically acceptable salt thereof,
from 70.0 to 90.0 parts by weight of a diluent,
from 1.0 to 3.0 parts by weight of a binder,
from 0.5 to 2.0 parts by weight of a basic additive,
from 2.0 to 5.0 parts by weight of a disintegrant,
from 0.5 to 2.0 parts by weight of a lubricant,
from 5.0 to 10.0 parts by weight of a coating agent, and
from 0.1 to 1.0 parts by weight of a coloring agent,
per 100 parts by weight of the pharmaceutical composition.

(23) The pharmaceutical composition according to the clause (21) or (22), further comprising an amount of from 0.01 to 1 parts by weight of a polishing agent per 100 parts by weight of the pharmaceutical composition.

(24) The pharmaceutical composition according to any one of the clauses (21) to (23), wherein the diluent is mannitol and/or crystalline cellulose, the binder is hydroxypropylcellulose, the basic additive is calcium carbonate, the disintegrant is croscarmellose sodium, the lubricant is magnesium stearate, the coating agent is one or more kinds of coating agent(s) selected from a water-soluble polymer, lactose and titanium oxide, and the coloring agent is yellow ferric oxide.

(25) The pharmaceutical composition according to the clause (24), wherein the water-soluble polymer is one or more kinds of water-soluble polymer(s) selected from polyvinyl alcohol-polyethylene glycol graft copolymer, hypromellose and polyethylene glycol.
(26) The pharmaceutical composition according to any one of the clauses (1) to (25), wherein the median diameter ($D_{90}$) of (4-{(3S)-3-[(1R)-1-(naphthalen-1-yl)ethylamino]pyrrolidin-1-yl}phenyl)acetic acid (Compound A) or a pharmacologically acceptable salt thereof is 75 μm or less.
(27) The pharmaceutical composition according to any one of the clauses (1) to (25), wherein the median diameter ($D_{90}$) of (4-{(3S)-3-[(1R)-1-(naphthalen-1-yl)ethylamino]pyrrolidin-1-yl}phenyl)acetic acid (Compound A) or a pharmacologically acceptable salt thereof is 50 μm or less.
(28) The pharmaceutical composition according to any one of the clauses (1) to (25), wherein the median diameter ($D_{90}$) of (4-{(3S)-3-[(1R)-1-(naphthalen-1-yl)ethylamino]pyrrolidin-1-yl}phenyl)acetic acid (Compound A) or a pharmacologically acceptable salt thereof is 35 μm or less.
(29) The pharmaceutical composition according to any one of the clauses (1) to (28), wherein the pharmaceutical composition is a composition for preventing or treating hyperparathyroidism.
(30) The pharmaceutical composition according to any one of the clauses (1) to (29), wherein the pharmaceutical composition is an oral formulation.
(31) The pharmaceutical composition according to any one of the clauses (1) to (30), wherein the pharmaceutical composition is a solid formulation.
(32) The pharmaceutical composition according to the clause (31), wherein the solid formulation is in the form of a tablet, powder, fine granule, granule, capsule or dry syrup.
(33) The pharmaceutical formulation according to the clause (31), wherein the solid formulation is a tablet.
(34) A blister pack product manufactured using the pharmaceutical composition according to any one of the clauses (1) to (33), a film laminated with a polymer and aluminum foil.
(35) The blister pack product according to the clause (34), wherein the film laminated with a polymer is a film laminated with one or more kinds of polymer(s) selected from polypropylene, polyvinyl chloride, polyvinylidene chloride and polychlorotrifluoroethylene.
(36) The blister pack product according to the clause (34) or (35), wherein the aluminum foil is an aluminum foil in which the quantity of melamine resin in an adhesive agent is reduced.
(37) A pharmaceutical packaging product, wherein the blister pack product according to any one of the clauses (34) to (36) is enclosed in the package.
(38) The pharmaceutical packaging product according to the clause (37), wherein the package is an aluminum bag.
(39) The pharmaceutical packaging product according to the clause (37) or (38), wherein a deoxidizer and/or desiccant are further enclosed in the package.

The present invention can provide a stable pharmaceutical composition and the like comprising an arylalkylamine compound that is useful for preventing or treating hyperparathyroidism and the like, and can be acceptable as a pharmaceutical product.

DETAILED DESCRIPTION OF THE INVENTION

The pharmaceutical composition of the present invention comprises Compound A as an arylalkylamine compound which is an active ingredient, or a pharmacologically acceptable salt thereof and a diluent.

The structure of Compound A in the present invention is as described above and Compound A can be manufactured by a method disclosed in WO 2005/115975 or by equivalent methods. The pharmacologically acceptable salt of Compound A includes alkali metal salt such as sodium salt, potassium salt; alkaline earth metal salt such as calcium salt, magnesium salt; organic base salt such as amine salt. Compound A of the present invention or a pharmacologically acceptable salt thereof includes either internal salt and addition products thereof, their solvate or hydrate and the like. In the pharmaceutical composition of the present invention, the amount of Compound A or a pharmacologically acceptable salt thereof is not particularly limited, but, for example, an amount of from 0.01 mg to 100 mg is preferably included in the pharmaceutical composition, more preferably from 0.1 mg to 20 mg, further preferably from 0.5 mg to 5 mg, and particularly preferably from 1 mg to 2 mg. In the pharmaceutical composition of the present invention, the amount of Compound A or a pharmacologically acceptable salt thereof is not particularly limited, but an amount of from 0.3 parts by weight to 5.0 parts by weight per 100 parts by weight of the pharmaceutical composition is preferably included, more preferably from 0.5 parts by weight to 5.0 parts by weight, further preferably from 0.5 parts by weight to 2.0 parts by weight, and further preferably from 0.5 parts by weight to 1.5 parts by weight. In addition, the size of Compound A or a pharmacologically acceptable salt thereof used in the pharmaceutical composition of the present invention is preferably 100 μm or less as the median diameter ($D_{90}$), more preferably 75 μm or less, further preferably 50 μm or less, and the most preferably 35 μm or less.

A diluent contained in the pharmaceutical composition of the present invention is not particularly limited as long as the diluent is the one used for medicine, but, for example, includes sugar, sugar alcohol, cellulose derivative, starch derivative, inorganic salt and the like, preferably lactose (more preferably lactose hydrate), white (refined) sugar, maltose, sucrose, mannitol (preferably D-mannitol), sorbitol, erythritol, maltitol, xylitol, glucose, crystalline cellulose, corn starch, potato starch, calcium monohydrogenphosphate, calcium dihydrogenphosphate, sodium dihydrogenphosphate, calcium phosphate and the like, and combination of two or more kinds of these diluents may be used. The diluent contained in the pharmaceutical composition of the present invention is preferably used in combination with mannitol (preferably D-mannitol) and crystalline cellulose. In the pharmaceutical composition of the present invention, the amount of the diluent is not particularly limited, but, for example, the diluent is preferably included in an amount of from 0.1 part by weight to 99.9 parts by weight, more preferably from 1 parts by weight to 95 parts by weight, and further preferably from 10 parts by weight to 90 parts by weight, per 100 parts by weight of the pharmaceutical composition. The pharmaceutical composition of the present invention may include other additives used as medicine other than Compound A and the diluent, for example, may include one or more kinds of additive(s) selected from binder, basic additive, disintegrant, lubricant, coloring agent and polishing agent used as pharmaceutical preparations. In addition, the binder, basic additive, disintegrant, lubricant, coloring agent, polishing agent according to the description are not limited to each applications (functions) previously described, respectively, but can be used for other applications (functions) (e.g., use of a binder as a diluent, use of a diluent as a binder and the like).

The binder in the present invention is not particularly limited as long as the binder is the one used for medicine, but, for example, includes cellulose derivatives such as hydroxypropylcellulose, hydroxypropylmethylcellulose, methylcellulose, carboxymethylcellulose, carboxymethylethylcellulose, hydroxyethylcellulose, hydroxypropylmethylcellulose acetate succinate, hydroxypropylmethylcellulose phthalate; hydroxypropyl starch, carboxyvinyl polymer, polyvinylpyrrolidone, polyvinyl alcohol, methacrylate copolymer, polyethylene glycol (macrogol), starch, gelatin, dextrin, pullulan, agar, gum Arabic and the like, preferably hydroxypropylcellulose, polyvinyl alcohol, polyvinylpyrrolidone and the like, and the combination of two or more these binders may be used. In the pharmaceutical composition of the present invention, the amount of the binder is not particularly limited, but, for example, the binder is preferably included in an amount of from 0.1 parts by weight to 10 parts by weight, more preferably from 0.5 parts by weight to 7 parts by weight, and further preferably from 1 part by weight to 5 parts by weight, per 100 parts by weight of the pharmaceutical composition.

The basic additive in the present invention is not particularly limited as long as the basic additive is the one used for medicine, but, for example, includes basic oxide, carbonate, hydrogencarbonate, silicate and salt of metasilicate aluminate and the like, wherein the basic oxide includes magnesium oxide and the like, the basic hydroxide includes magnesium hydroxide, aluminum hydroxide and the like, the carbonate includes magnesium carbonate, calcium carbonate and the like, the hydrogencarbonate includes sodium hydrogencarbonate and the like, the silicate includes calcium silicate and the like, the salt of metasilicate aluminate includes magnesium aluminometasilicate and the like. Among these basic additives, magnesium carbonate, calcium silicate, magnesium aluminometasilicate, calcium carbonate and the like are preferable, calcium carbonate is more preferable, and a combination of two or more kinds of these basic additives may be used. In the pharmaceutical composition of the present invention, the amount of the basic additive is not particularly limited, but, for example, the basic additive is preferably included in an amount of from 0.01 parts by weight to 50 parts by weight, more preferably from 0.1 parts by weight to 30 parts by weight, and further preferably from 0.5 parts by weight to 10 parts by weight, per 100 parts by weight of the pharmaceutical composition.

The disintegrant in the present invention is not particularly limited as long as the disintegrant is the one used for medicine, but, for example, includes croscarmellose sodium, crospovidone, sodium carboxymethyl starch, low-substituted hydroxypropylcellulose, carboxymethyl cellulose, carboxymethylcellulose calcium, partially pregelatinized starch, starch and the like, preferably croscarmellose sodium, crospovidoneuse and the like, and a combination of two or more kinds of these disintegrants may be used. In the pharmaceutical composition of the present invention, the amount of the disintegrant is not particularly limited, but, for example, it is preferably included in an amount of from 0.5 parts by weight to 20 parts by weight, more preferably from 1 part by weight to 15 parts by weight, and further preferably from 3 parts by weight to 10 parts by weight, per 100 parts by weigh of the pharmaceutical composition.

The lubricant in the present invention is not particularly limited as long as the lubricant is the one used for medicine, but, for example, preferably includes magnesium stearate, calcium stearate, talc, glyceryl monostearate, light anhydrous silicic acid, sodium stearyl fumarate, sucrose fatty acid esters (e.g., sucrose stearate, sucrose palmitate, sucrose oleate, sucrose laurate and the like), and a combination of two or more kinds of these lubricants may be used. In the pharmaceutical composition of the present invention, the amount of the lubricant is not particularly limited, but, for example, the lubricant is preferably included in an amount of from 0.05 parts by weight to 10 parts by weight, more preferably from 0.1 parts by weight to 5 parts by weight, and further preferably from 0.5 parts by weight to 3 parts by weight, per 100 parts by weight of the pharmaceutical composition.

The coloring agent in the present invention is not particularly limited as long as the coloring agent is the one used for medicine, but, for example, includes yellow ferric oxide, titanium oxide, talc, ferric oxide, black iron oxide, copper chlorophyll, sodium copper chlorophylline, carbon black, medicinal charcoal, food dye, licorice extract, green tea powder, riboflavin, riboflavin butyrate, riboflavin sodium phosphate, octyldodecyl myristate and the like, preferably yellow ferric oxide, titanium oxide, talc, ferric oxide, and the like, and a combination of two or more kinds of these coloring agents may be used. In the pharmaceutical composition of the present invention, the amount of the coloring agent is not particularly limited, but, for example, the coloring agent is preferably included in an amount of from 0.0001 parts by weight to 10000 parts by weight, more preferably from 0.01 parts by weight to 1000 parts by weight, and further preferably from 0.1 parts by weight to 500 parts by weight, per 100 parts by weight of Compound A or a pharmacologically acceptable salt thereof.

The polishing agent of the present invention is not particularly limited as long as the polishing agent is the one used for medicine, but, for example, preferably includes carnauba wax, shellac, beeswax, hardened oil, magnesium stearate and the like, and a combination of two or more kinds of these polishing agents may be used. The amount of the polishing agent of the present invention is not particularly limited, but, for example, the polishing agent is included preferably in an amount of from 0.0001 parts by weight to 100 parts by weight, more preferably from 0.001 parts by weight to 10 parts by weight, and further preferably 0.01 parts by weight to 1 part by weight, per 100 parts by weight of the pharmaceutical composition.

The diluent, binder, basic additive, disintegrant, lubricant, coloring agent and polishing agent in the present invention include hydrate, solvate, and salt thereof.

The pharmaceutical composition of the present invention may not have a coating film (coating), but it is preferable to have a coating film (coating) for the purpose of providing photostability/preservation stability toward temperature/humidity to the pharmaceutical composition. The coating film can be provided by treating the pharmaceutical composition of the present invention with a coating process. The coating process can be performed by spraying a coating solution containing a coating agent onto an uncoated preparation containing Compound A and the like in a spray coating method and the like. The coating agent is used by dissolving, suspending, and dispersing it into a coating solution. A solvent for constituting the coating solution includes water, alcohols such as methanol, ethanol, and is more preferably water. An ingredient constituting the coating agent is not particularly limited, but, for example, includes a water-soluble polymer, lactose, white (refined) sugar, titanium oxide, talc, polyvinylpyrrolidone and the like, wherein the water-soluble polymer includes polyvinyl alcohol-polyethylene glycol graft copolymer, polyvinylpyrrolidone, hypromellose, hydroxypropylcellulose, polyvinyl alcohol, polyvinyl alcohol-acrylic acid-methyl methacrylate copolymer, polyethylene glycol and the like. The amount of the coating agent is not particularly limited, but, for example, the coating agent is preferably included in an amount of from 0.1 parts by weight to 100 parts by weight, more preferably from 0.5 parts by weight to 80 parts by weight, and further preferably from 1 part by weight to 60 parts by weight, per 100 parts by weight of the coating film. The amount of the coating solution used for the coating process is not particularly limited as long as it provides photostability and the like to the pharmaceutical composition, and it is preferably included in an amount of from 0.01 parts by weight to 90 parts by weight of the coating film (coating) in the dry state, more preferably from 0.05 parts by weight to 70 parts by weight, and further preferably from 0.1 parts by weight to 50 parts by weight, per 100 parts by weight of a uncoated formulation (formulation not subjected to coating process). The pharmaceutical composition of the present invention preferably contains the first coating film and the second coating film, wherein the first coating film preferably contains a polyvinyl alcohol-polyethylene glycol graft copolymer and the second coating film preferably contains one or more kinds of coating agent(s) selected from a water-soluble polymer, lactose, white (refined) sugar, titanium oxide and talc, and more preferably one or more kinds of coating agent(s) selected from a water-soluble polymer, lactose and titanium oxide. According to another embodiment of the pharmaceutical composition of the present invention, it is preferable that the second coating film contains a coloring agent.

According to a preferred embodiment of the pharmaceutical composition of the present invention, provided is a pharmaceutical composition comprising an amount of from 0.5 to 5.0 parts by weight of (4-{(3S)-3-[(1R)-1-(naphthalen-1-yl)ethylamino]pyrrolidin-1-yl}phenyl)acetic acid (Compound A) or a pharmacologically acceptable salt thereof, from 50.0 to 90.0 parts by weight of a diluent, from 1.0 to 5.0 parts by weight of a binder, from 0.5 to 5.0 parts by weight of a basic additive, from 2.0 to 10.0 parts by weight of a disintegrant, from 0.5 to 3.0 parts by weight of a lubricant, from 3.0 to 10.0 parts by weight of a coating agent and from 0.1 to 1.0 parts by weight of a coloring agent, per 100 parts by weight of the pharmaceutical composition. Herein, according to a preferred embodiment, the diluent is mannitol and/or crystalline cellulose, the binder is hydroxypropylcellulose, the basic additive is calcium carbonate, the disintegrant is croscarmellose sodium, the lubricant is magnesium stearate and the coating agent is one or more kinds of coating agent(s) selected from a water-soluble polymer, lactose and titanium oxide, and the coloring agent is yellow ferric oxide.

According to a preferred embodiment of the pharmaceutical composition of the present invention, provided is a pharmaceutical composition comprising an amount of from 0.5 to 5.0 parts by weight of (4-{(3S)-3-[(1R)-1-(naphthalen-1-yl)ethylamino]pyrrolidin-1-yl}phenyl)acetic acid (Compound A) or a pharmacologically acceptable salt thereof, from 50.0 to 89.0 parts by weight of a diluent, from 1.0 to 5.0 parts by weight of a binder, from 0.5 to 5.0 parts by weight of a basic additive, from 3.0 to 10.0 parts by weight of a disintegrant, from 0.5 to 3.0 parts by weight of a lubricant, from 3.0 to 10.0 parts by weight of a coating agent and from 0.1 to 1.0 parts by weight of a coloring agent, per 100 parts by weight of the pharmaceutical composition. Herein, according to a preferred embodiment, the diluent is mannitol and/or crystalline cellulose, the binder is hydroxypropylcellulose, the basic additive is calcium carbonate, the disintegrant is croscarmellose sodium, the lubricant is magnesium stearate and the coating agent is one or more kinds of coating agent(s) selected from a water-soluble polymer, lactose and titanium oxide, and the coloring agent is yellow ferric oxide.

According to another preferred embodiment of the pharmaceutical composition of the present invention, provided is a pharmaceutical composition comprising an amount of from 0.5 to 2.0 parts by weight of (4-{(3S)-3-[(1R)-1-(naphthalen-1-yl)ethylamino]pyrrolidin-1-yl}phenyl)acetic acid (Compound A) or a pharmacologically acceptable salt thereof, from 70.0 to 90.0 parts by weight of a diluent, from 1.0 to 3.0 parts by weight of a binder, from 0.5 to 2.0 parts by weight of a basic additive, from 2.0 to 5.0 parts by weight of a disintegrant, from 0.5 to 2.0 parts by weight of a lubricant, from 5.0 to 10.0 parts by weight of a coating agent and 0.1 to 1.0 parts by weight of a coloring agent, per 100 parts by weight of the pharmaceutical composition. Herein, according to a preferred embodiment, the diluent is mannitol and/or crystalline cellulose, the binder is hydroxypropylcellulose, the basic additive is calcium carbonate, the disintegrant is croscarmellose sodium, the lubricant is magnesium stearate, the coating agent is one or more kinds of coating agent(s) selected from a water-soluble polymer, lactose and titanium oxide and the coloring agent is yellow ferric oxide.

According to another preferred embodiment of the pharmaceutical composition of the present invention, provided is a pharmaceutical composition comprising an amount of from 0.5 to 2.0 parts by weight of (4-{(3S)-3-[(1R)-1-(naphthalen-1-yl)ethylamino]pyrrolidin-1-yl}phenyl)acetic acid (Compound A) or a pharmacologically acceptable salt thereof, from 70.0 to 89.0 parts by weight of a diluent, from 1.0 to 3.0 parts by weight of a binder, from 0.5 to 2.0 parts by weight of a basic additive, from 3.0 to 5.0 parts by weight of a disintegrant, from 0.5 to 2.0 parts by weight of a lubricant, from 5.0 to 10.0 parts by weight of a coating agent and from 0.1 to 1.0 parts by weight of a coloring agent, per 100 parts by weight of the pharmaceutical composition. Herein, according to a preferred embodiment, the diluent is mannitol and/or crystalline cellulose, the binder is hydroxypropylcellulose, the basic additive is calcium carbonate, the disintegrant is croscarmellose sodium, the lubricant is magnesium stearate and the coating agent is one or more kinds of coating agent(s) selected from a water-soluble polymer, lactose and titanium oxide, and the coloring agent is yellow ferric oxide.

According to another preferred embodiment of the pharmaceutical composition of the present invention, provided is a pharmaceutical composition comprising an amount of from 0.3 to 5.0 parts by weight (preferably from 0.5 to 5.0 parts by weight, more preferably from 0.5 to 2.0 parts by weight, and further preferably from 0.5 to 1.5 parts by weight) of (4-{(3S)-3-[(1R)-1-(naphthalen-1-yl)ethylamino]pyrrolidin-1-yl}phenyl)acetic acid (Compound A) or a pharmacologically acceptable salt thereof, from 50.0 to 70.0 parts by weight (preferably from 50.0 to 60.0 parts by weight) of mannitol (preferably D-mannitol) as a diluent, and from 20.0 to 40.0 parts by weight (preferably from 20.0 to 30.0 parts by weight) of crystalline cellulose as a diluent, per 100 parts by weight of the pharmaceutical composition. Compound A or a pharmacologically acceptable salt thereof can be stabilized by concomitantly containing mannitol and crystalline cellulose as a diluent.

According to another preferred embodiment of the pharmaceutical composition of the present invention, provided is a pharmaceutical composition comprising an amount of from 0.3 to 5.0 parts by weight (preferably from 0.5 to 5.0 parts by weight, more preferably from 0.5 to 2.0 parts by weight, and further preferably from 0.5 to 1.5 parts by weight) of (4-{(3S)-3-[(1R)-1-(naphthalen-1-yl)ethylamino]pyrrolidin-1-yl}phenyl)acetic acid (Compound A) or a pharmacologically acceptable salt thereof, from 50.0 to 70.0 parts by weight (preferably from 50.0 to 60.0 parts by weight) of mannitol (preferably D-mannitol) as a diluent, from 20.0 to 40.0 parts by weight (preferably from 20.0 to 30.0 parts by weight) of crystalline cellulose as a diluent, and from 3.0 to 10.0 parts by weight (preferably from 3.0 to 5.0 parts by weight) of croscarmellose sodium as a disintegrant, per 100 parts by weight of the pharmaceutical composition.

According to another preferred embodiment of the pharmaceutical composition of the present invention, provided is a pharmaceutical composition comprising an amount of from 0.3 to 5.0 parts by weight (preferably from 0.5 to 5.0 parts by weight, more preferable from 0.5 to 2.0 parts by weight, and further preferably from 0.5 to 1.5 parts by weight) of (4-{(3S)-3-[(1R)-1-(naphthalen-1-yl)ethylamino]pyrrolidin-1-yl}phenyl)acetic acid (Compound A) or a pharmacologically acceptable salt thereof, from 50.0 to 70.0 parts by weight (preferably from 50.0 to 60.0 parts by weight) of mannitol (preferably D-mannitol) as a diluent, from 20.0 to 40.0 parts by weight (preferably from 20.0 to 30.0 parts by weight) of crystalline cellulose as a diluent, and from 0.5 to 5.0 parts by weight (preferably from 0.5 to 2.0 parts by weight) of calcium carbonate as a basic additive, per 100 parts by weigh of the pharmaceutical composition.

According to another preferred embodiment of the pharmaceutical composition of the present invention, provided is a pharmaceutical composition comprising an amount of from 0.3 to 5.0 parts by weight (preferably from 0.5 to 5.0 parts by weight, more preferable from 0.5 to 2.0 parts by weight, and further preferably from 0.5 to 1.5 parts by weight) of (4-{(3S)-3-[(1R)-1-(naphthalen-1-yl)ethylamino]pyrrolidin-1-yl}phenyl)acetic acid (Compound A) or a pharmacologically acceptable salt thereof, from 50.0 to 70.0 parts by weight (preferably 50.0 to 60.0 parts by weight) of mannitol (preferably D-mannitol) as a diluent, from 20.0 to 40.0 parts by weight (preferably from 20.0 to 30.0 parts by weight) of crystalline cellulose as a diluent, from 0.5 to 5.0 parts by weight (preferably from 0.5 to 2.0 parts by weight) of calcium carbonate as a basic additive, and from 3.0 to 10.0 parts by weight (preferably from 4.0 to 7.0 parts by weight) of a water-soluble polymer (preferably a polyvinyl alcohol-polyethylene glycol graft copolymer, hypromellose, polyethylene glycol or a mixture thereof) as a coating agent, per 100 parts by weight of the pharmaceutical composition.

According to another preferred embodiment of the pharmaceutical composition of the present invention, provided is a pharmaceutical composition comprising an amount of from 0.3 to 5.0 parts by weight (preferably from 0.5 to 5.0 parts by weight, more preferable from 0.5 to 2.0 parts by weight, and further preferably from 0.5 to 1.5 parts by weight) of (4-{(3S)-3-[(1R)-1-(naphthalen-1-yl)ethylamino]pyrrolidin-1-yl}phenyl)acetic acid (Compound A) or a pharmacologically acceptable salt thereof, from 50.0 to 70.0 parts by weight (preferably from 50.0 to 60.0 parts by weight) of mannitol (preferably D-mannitol) as a diluent, from 20.0 to 40.0 parts by weight (preferably from 20.0 to 30.0 parts by weight) of crystalline cellulose as a diluent, from 0.5 to 5.0 parts by weight (preferably from 0.5 to 2.0 parts by weight) of calcium carbonate as a basic additive, from 0.5 to 5.0 parts by weight (preferably from 1.0 to 2.0 parts by weight) of a water-soluble polymer (preferably a polyvinyl alcohol-polyethylene glycol graft copolymer) as a coating agent (the first coating film), and from 0.5 to 5.0 parts by weight (preferably from 1.0 to 3.1 parts by weight) of a water-soluble polymer (preferably hypromellose, polyethylene glycol (for example, macrogol), and/or a mixture thereof), per 100 parts by weight of the pharmaceutical composition.

According to another preferred embodiment of the pharmaceutical composition of the present invention, provided is a pharmaceutical composition comprising an amount of from 0.3 to 5.0 parts by weight (preferably from 0.5 to 5.0 parts by weight, and more preferable from 0.5 to 2.0 parts by weight, further preferably from 0.5 to 1.5 parts by weight) of (4-{(3S)-3-[(1R)-1-(naphthalen-1-yl)ethylamino]pyrrolidin-1-yl}phenyl)acetic acid (Compound A) or a pharmacologically acceptable salt thereof, from 50.0 to 70.0 parts by weight (preferably from 50.0 to 60.0 parts by weight) of mannitol (preferably D-mannitol) as a diluent, from 20.0 to 40.0 parts by weight (preferably from 20.0 to 30.0 parts by weight) of crystalline cellulose as a diluent, and from 1.0 to 5.0 parts by weight (preferably from 1.0 to 3.0 parts by weight) of hydroxypropylcellulose as a binder, per 100 parts by weight of the pharmaceutical composition.

According to another preferred embodiment of the pharmaceutical composition of the present invention, provided is a pharmaceutical composition comprising from 0.3 to 5.0 parts by weight (preferably from 0.5 to 5.0 parts by weight, more preferable from 0.5 to 2.0 parts by weight, and further preferably 0.5 to 1.5 parts by weight) of (4-{(3S)-3-[(1R)-1-(naphthalen-1-yl)ethylamino]pyrrolidin-1-yl}phenyl)acetic acid (Compound A) or a pharmacologically acceptable salt thereof, from 50.0 to 70.0 parts by weight (preferably from 50.0 to 60.0 parts by weight) of mannitol (preferably D-mannitol) as a diluent, from 20.0 to 40.0 parts by weight (preferably from 20.0 to 30.0 parts by weight) of crystalline cellulose as a diluent, and from 0.5 to 3.0 parts by weight (preferably from 0.5 to 2.0 parts by weight) of magnesium stearate as a polishing agent, per 100 parts by weight of the pharmaceutical composition.

According to another preferred embodiment of the pharmaceutical composition of the present invention, provided is a pharmaceutical composition comprising from 0.3 to 5.0 parts by weight (preferably from 0.5 to 5.0 parts by weight, more preferably from 0.5 to 2.0 parts by weight, and further preferably from 0.5 to 1.5 parts by weight) of (4-{(3S)-3-[(1R)-1-(naphthalen-1-yl)ethylamino]pyrrolidin-1-yl}phenyl)acetic acid (Compound A) or a pharmacologically acceptable salt thereof, from 50.0 to 70.0 parts by weight (preferably from 50.0 to 60.0 parts by weight) of mannitol (preferably D-mannitol) as a diluent, from 20.0 to 40.0 parts by weight (preferably from 20.0 to 30.0 parts by weight) of crystalline cellulose as a diluent, and from 3.0 to 10.0 parts by weight (preferably from 4.0 to 7.0 parts by weight) of a water-soluble polymer (preferably a polyvinyl alcohol-polyethylene glycol graft copolymer, hypromellose, polyethylene glycol or a mixture thereof) as a coating agent, per 100 parts by weight of the pharmaceutical composition.

According to another preferred embodiment of the pharmaceutical composition of the present invention, provided is a pharmaceutical composition comprising an amount of from 0.3 to 5.0 parts by weight (preferably from 0.5 to 5.0 parts by weight, more preferable from 0.5 to 2.0 parts by weight, and further preferably from 0.5 to 1.5 parts by weight) of (4-{(3S)-3-[(1R)-1-(naphthalen-1-yl)ethylamino]pyrrolidin-1-yl}phenyl)acetic acid (Compound A) or a pharmacologically acceptable salt thereof, from 50.0 to 70.0 parts by weight (preferably from 50.0 to 60.0 parts by weight) of mannitol (preferably D-mannitol) as a diluent, from 20.0 to 40.0 parts by weight (preferably from 20.0 to 30.0 parts by weight) of crystalline cellulose as a diluent, from 0.5 to 5.0 parts by weight (preferably from 1.0 to 2.0 parts by weight) of a water-soluble polymer (preferably a polyvinyl alcohol-polyethylene glycol graft copolymer) as a coating agent (the first coating film), and from 0.5 to 5.0 parts by weight (preferably from 1.0 to 3.1 parts by weight) of a water-soluble polymer (preferably hypromellose, polyethylene glycol and/or a mixture thereof) as a coating agent (the second coating film), per 100 parts by weight of pharmaceutical composition.

The pharmaceutical composition of the present invention, for example, can be used to prevent or treat hyperparathyroidism, hypercalcemia in parathyroid cancer or primary hyperparathyroidism in case of inoperable parathyroidectomy or postoperative recurrence, and preferably can be used to prevent and treat hyperparathyroidism (more preferably secondary hyperparathyroidism).

The pharmaceutical composition of the present invention may be either an oral formulation or non-oral formulation, and preferably an oral formulation, wherein a coloring agent, a flavor improvement agent and the like can further be added to this oral formulation.

The formulation of the pharmaceutical composition of the present invention is not particularly limited, but it is preferable to be a solid formulation, more preferably a tablet, powder, fine granule, granule and, a capsule or dry syrup, and it is further preferable to be a tablet.

The method for manufacturing the pharmaceutical composition of the present invention is not particularly limited, but, for example, it can be produced by commonly used methods in technical fields of pharmaceuticals such as a compression-molding method and the like. For example, it can be produced by using wet granulation such as extrusion granulation (by a screw-extruder type granulator, roll-extruder type granulator), a rolling granulation method (by a rolling drum type granulator, centrifugal tumbling granulator), a fluidized-bed granulation method (by a fluidized-bed granulator, tumbling fluidized-bed granulator), a stirring granulation method (by a stirring granulator) and the like. In either case, for example, it is preferable to apply a method in which Compound A or a pharmacologically acceptable salt thereof and additive are mixed, a solvent or a binder solution is added to the mixture obtained to form granulates, and the granulates obtained are dried. Solvents used include, for example, water, ethanol, isopropyl alcohol, a mixture of these solvents and the like, and a binder solution includes, for example, a solution prepared by dissolving a binder in water, ethanol, isopropyl alcohol, or a mixture of these solvents, but an aqueous solution of the binder is the most suitable. Next, for example, preparation of a tablet may be performed in a process whereby the dried granules obtained are formulated using a compression tableting machine. The pressure of tableting, for example, can be properly chosen within the range of 300 to 3000 kg/cm$^2$. The tablet size is not particularly limited, but, for example, is preferably 5 to 15 mm in diameter, wherein the weight per tablet is from 20 to 3000 mg. When a tablet is subjected to a coating process, the process includes a method whereby the tablet obtained (uncoated tablet) is coated with a solution or dispersion in which a coating composition is dissolved/dispersed to form a coating film. Solvents for dissolving/dispersing the coating composition include, for example, water, ethanol, isopropyl alcohol, or a mixed solvent thereof; and among them all, water is preferable. For example, coating is performed using a conventional pan-style coating machine, a vented coating machine, a fluidized bed-type coating device, or a tumbling fluidized bed-type coating device.

The blister pack product of the present invention is manufactured using a pharmaceutical composition comprising Compound A described above and the like and a film laminated with a polymer and aluminum foil. The film laminated with the polymer is not particularly limited as long as it is commonly used for blister pack products, but a film and the like laminated with polymers such as polypropylene, polyvinyl chloride, polyvinylidene chloride, polychlorotrifluoroethylene and the like are preferable. The aluminum foil is not particularly limited as long as it is commonly used for blister pack products, and common general-purpose aluminum foil may be used, but it is preferable to use aluminum foil in which the amount of melamine resin in an adhesive agent is reduced. The manufacturing method of the blister pack product of the present invention is not particularly limited, but the blister pack product is obtained by making a pocket on a film laminated with a polymer by using a conventionally used blister packaging machine, followed by incorporating a tablet and sealing aluminum foil by heat and the like.

The pharmaceutical packaging product of the present invention encloses the blister pack product in a package. The package is not particularly limited as long as it is commonly used for pharmaceutical packaging products, but an aluminum bag and the like are preferable. The pharmaceutical packaging product may enclose a material which is commonly enclosed in pharmaceutical packaging products together. It is preferable that a deoxidizer and/or a desiccating agent are enclosed with the blister packing product together. The pharmaceutical packaging product of the present invention can be produced by enclosing the blister pack product manufactured as above in a package such as an aluminum bag, and then sealing the package using a heat sealer and the like.

According to another embodiment of the present invention, provided is a method for treating or preventing comprising administering a composition comprising the effective dose of (4-{(3S)-3-[(1R)-1-(naphthalen-1-yl)ethylamino]pyrrolidin-1-yl}phenyl)acetic acid or a pharmacologically acceptable salt thereof and a diluent to a subject (preferably the subject who requires it). The method of treatment or prevention is preferably a method for treating or preventing hyperparathyroidism.

According to another embodiment of the present invention, provided is a composition comprising 4-{(3S)-3-[(1R)-1-(naphthalen-1-yl)ethylamino]pyrrolidin-1-yl}phenyl)acetic acid or a pharmacologically acceptable salt thereof and a diluent for the use as a medicine.

According to another embodiment of the present invention, provided is a composition comprising 4-{(3S)-3-[(1R)-1-(naphthalen-1-yl)ethylamino]pyrrolidin-1-yl}phenyl)acetic acid or a pharmacologically acceptable salt thereof and a diluent for the use of the treatment or prevention of hyperparathyroidism.

According to another embodiment of the present invention, the use of a composition comprising 4-{(3S)-3-[(1R)-1-(naphthalen-1-yl)ethylamino]pyrrolidin-1-yl}phenyl)acetic acid or a pharmacologically acceptable salt thereof and a diluent is provided in the manufacture of a medicine for treating or preventing hyperparathyroidism.

According to another embodiment of the present invention, provided is the use of a composition comprising 4-{(3S)-3-[(1R)-1-(naphthalen-1-yl)ethylamino]pyrrolidine-1-yl}phenyl)acetic acid or a pharmacologically acceptable salt thereof and a diluent for treating or preventing hyperparathyroidism.

Herein, the diluent contained in the composition mentioned above may be the same as the diluent contained in the pharmaceutical composition of the present invention, and further may include one or more kinds of additive(s) selected from binder, basic additive, disintegrant, lubricant, coloring agent and polishing agent, just as with the pharmaceutical composition of the present invention. Also, the above-mentioned composition can be used for hypercalcemia in parathyroid cancer or primary hyperparathyroidism in case of inoperable parathyroidectomy or postoperative recurrence, just as with the pharmaceutical composition of the present invention.

According to another embodiment of the present invention, provided is a stabilization method of (4-{(3S)-3-[(1R)-1-(naphthalen-1-yl)ethylamino]pyrrolidin-1-yl}phenyl)acetic acid or a pharmacologically acceptable salt thereof characterized by incorporating a diluent with (4-{(3S)-3-[(1R)-1-(naphthalen-1-yl)ethylamino]pyrrolidin-1-yl}phenyl)acetic acid or a pharmacologically acceptable salt thereof. Herein, stabilization means that, when (4-{(3S)-3-[(1R)-1-(naphthalen-1-yl)ethylamino]pyrrolidin-1-yl}phenyl)acetic acid or a pharmacologically acceptable salt thereof is stored for a long time (e.g., at 60° C. for one month), production of related substances is more suppressed as compared to the case without a diluent. Therefore, according to another preferred embodiment, provided is a method of suppressing the production of related substances of (4-{(3S)-3-[(1R)-1-(naphthalen-1-yl)ethylamino]pyrrolidin-1-yl}phenyl)acetic acid or a pharmacologically acceptable salt thereof characterized by incorporating a diluent with (4-{(3S)-3-[(1R)-1-(naphthalen-1-yl)ethylamino]pyrrolidin-1-yl}phenyl)acetic acid or a pharmacologically acceptable salt thereof. Herein, in the stabilizing method of the present invention, one or more kinds of additive(s) selected from binder, basic additive, disintegrant, lubricant, coloring agent and polishing agent may be used for further stabilization just as with the pharmaceutical composition of the present invention.

EXAMPLES

Next, the present invention will be specifically explained by Examples and Test Examples, but the present invention is not limited to these descriptions. In addition, in the related description of the following Examples, "(4-{(3S)-3-[(1R)-1-(naphthalen-1-yl)ethylamino]pyrrolidin-1-yl}phenyl)acetic acid is referred to as "Compound A". Compound A can be obtained by a method described in WO 2005/115975. In addition, "an A form crystal" of Compound A described in WO 2015/034031 was used as Compound A used in the following Examples.

Example 1-1

Preparation of a Tablet Using Mannitol as a Diluent

In a fluidized-bed granulator (FLO-5, Freund Corporation), 45.0 g of Compound A, 3757.5 g of D-mannitol (Japanese Pharmacopoeia, the same shall apply hereinafter), 1462.5 g of crystalline cellulose (CEOLUS PH301 (registered trademark), Asahi Kasei Chemicals Corporation, the same shall apply hereinafter) and 292.5 g of croscarmellose sodium (Ac-Di-Sol, FMC, the same shall apply hereinafter) were charged, and the mixture was mixed and granulated by spraying 2094 g of 8% by weight of hydroxypropylcellulose aqueous solution (HPC-L, Nippon Soda Co., Ltd., the same shall apply hereinafter) to obtain granulated granules after drying. The granulated granules obtained were sieved through a sizer (Comil QC-197S, Powrex) to obtain uniformly sized granules. The uniformly sized granules obtained (5450 g) and magnesium stearate (111.2 g) were mixed to obtain granules for tableting. The granules for tableting obtained were tableted using a tableting machine (Correct 12, made by Kikusui Seisakusho, LTD.) to obtain an uncoated tablet. A coating mixture 1 [containing 52.0 g of hypromellose (substitution degree: 2910, viscosity: 3 mPa·s) (Japanese Pharmacopoeia), 23.25 g of titanium oxide (Japanese Pharmacopoeia), 14.0 g of Macrogol 6000 (Japanese Pharmacopoeia), 10.0 g of lactose hydrate (Japanese Pharmacopoeia), 0.5 g of yellow ferric oxide (Japanese Pharmaceutical Excipients), and 0.25 g of ferric oxide (Japanese Pharmaceutical Excipients) in 100 g of the coating mixture 1] was dispersed in purified water to prepare a coating solution having a solid component concentration of 10% by weight. The desired tablet was obtained by coating 4885 g of an uncoated tablet using a tablet coating machine (HC-Multi, Freund Corporation) with the coating film adjusted to 5 parts by weight in the dry state per 100 parts by weight of the uncoated tablet.

Example 1-2

Preparation of a Tablet Using Lactose as a Diluent

In a fluidized-bed granulator (MP-01, Powrex), 10.0 g of Compound A, 1043.0 g of lactose hydrate (Japanese Pharmacopoeia, the same shall apply hereinafter) and 195.0 g of low-substituted hydroxypropylcellulose (L-HPC, Shin-Etsu Chemical Co., Ltd., the same shall apply hereinafter) were charged, the mixture was mixed and granulated by spraying 487.5 g of a HPC-L aqueous solution to obtain granulated granules after drying. The granulated granules obtained were sieved by a sieve with mesh opening of 710 μm to obtain uniformly sized granules. The uniformly sized granules obtained (1089 g) and magnesium stearate (11 g, Parteck LUB MST, Merck, the same shall apply hereinafter) were mixed to obtain granules for tableting. The granules for tableting obtained were tableted using a tablet machine (Correct 12, made by Kikusui Seisakusho, LTD.) to obtain an uncoated tablet (mass: 130 mg, tablet shape: circular (7 mm in diameter), the same shall apply hereinafter). A coating mixture 1 (containing the same composition mentioned above) was dispersed in purified water to prepare a coating solution containing 10% by weight of solid content concentration. The desired tablet was obtained by coating 200 g of an uncoated tablet using a tablet coating machine (DRC-200, Powrex) with the coating film adjusted to 4 parts by weight in the dry state per 100 parts by weight of the uncoated tablet.

The compositions of each ingredient in the tablet obtained in Examples 1-1 and 1-2 are shown in the following Table 1.

TABLE 1

| Ingredient | Example 1-1 | Example 1-2 |
|---|---|---|
| Compound A (mg) | 1.0 | 1.0 |
| Lactose hydrate (mg) | — | 104.3 |

TABLE 1-continued

| Ingredient | Example 1-1 | Example 1-2 |
|---|---|---|
| D-mannitol (mg) | 83.5 | — |
| Crystalline cellulose (mg) | 32.5 | — |
| Low-substituted hydroxypropylcellulose (mg) | — | 19.5 |
| Croscarmellose sodium (mg) | 6.5 | — |
| Hydroxypropylcellulose (mg) | 3.9 | 3.9 |
| Magnesium stearate (mg) | 2.6 | 1.3 |
| Coating mixture 1 (mg) | 6.5 | 5.2 |
| Total (mg) | 136.5 | 135 |

Test Example 1

The tablets obtained in Examples 1-1 and 1-2 were placed in a glass bottle (open) and stored under the conditions of 60° C. for one month, and production of related substances was evaluated according to the measurement conditions (measurement condition 1) described as follows. The results are shown in Table 3. At RRT (relative retention time) of 0.45, the production of related substances was not observed in the preparation obtained in Example 1-1, and very little production of related substances was found in the preparation obtained in Example 1-2. From these results, it can be understood that good preservation stability is obtained by the addition of D-mannitol or lactose hydrate as the diluent. Herein, RRT (relative retention time) means relative retention time of the related substances relative to the retention time of Compound A.

(Measurement Condition 1)

Detector: Ultraviolet absorption photometer (measurement wavelength: 220 nm)

Column: L-column2 (CERI) 4.6 mm I.D.×150 mm

Column temperature: Constant temperature at approximately 40° C.

Mobile phase A: water/acetonitrile/trifluoroacetic acid (1900/100/1)

Mobile phase B: acetonitrile/water/trifluoroacetic acid (1800/200/1)

Flow rate: 1.0 mL/min

Method for feeding Mobile phase solutions: The mixing ratio between Mobile phase A and Mobile phase B was changed as follows to control a concentration gradient for feeding solution.

TABLE 2

| Concentration gradient of mobile phase | | |
|---|---|---|
| Period after injection (minute) | Mobile phase A (vol %) | Mobile phase B (vol %) |
| 0-80 | 95 → 35 | 5 → 65 |
| 80-90 | 35 | 65 |
| 90-90.1 | 35 → 95 | 65 → 5 |
| 90.1-105 | 95 | 5 |

TABLE 3

| Production of related substances (Relative Retention Time (RRT): 0.45, Storage condition: 60° C., Glass bottle (Open)) | | |
|---|---|---|
| Storage period | Example 1-1 | Example 1-2 |
| At the onset | ND | ND |
| One month | ND | 0.32% |

ND: Below the detection limit.

Example 2-1

Preparation of a Tablet with the Addition of Crystalline Cellulose and an Aluminum Bag Packaged Product Thereof In a fluidized-bed granulator (MP-01, Powrex), 3.8 g of Compound A, 646.2 g of D-mannitol, 250.0 g of crystalline cellulose (MCC, CEOLUS PH301 (registered trademark), Asahi Kasei Chemicals Corporation, the same shall apply hereinafter) and 30.0 g of croscarmellose sodium were charged, the mixture was mixed and granulated by spraying 375.0 g of 8% by weight hydroxypropylcellulose aqueous solution to obtain granulated granules after drying. A tablet was obtained using the granulated granules obtained by the same method as described in Example 1-1. The tablet obtained was packaged to obtain a blister pack product using a semiautomatic PTP sheet preparation machine (FABN-TASY, O.M.A.R, the same shall apply hereinafter) using a polypropylene sheet (TAS-2230V, Taisei Chemical Industries, Ltd., the same shall apply hereinafter) and aluminum foil (UACJ) in which the amount of melamine resin in the adhesive is reduced. The blister pack product obtained was placed in an aluminum bag (HOSOKAWA YOKO Co., Ltd.) and the aluminum bag was sealed using a heat sealer (quick Sheeler, Shiga Hosoki, Co. Ltd., the same shall apply hereinafter) to obtain the desired aluminum bag packaged product.

Example 2-2

Preparation of a Tablet with the Addition of Crystalline Cellulose and an Aluminum Bag Packaged Product Thereof A tablet was prepared in the same way as described in Example 2-1. Furthermore, the desired aluminum bag packaged product was obtained from the tablet obtained using a sheet made of polypropylene and general-purpose aluminum foil (UACJ) by the same method as described in Example 2-1.

Example 3-1

Preparation of a Tablet with the Addition of Crystalline Cellulose and an Aluminum Bag Packaged Product Thereof A tablet was prepared using 3.8 g of Compound A, 746.2 g of D-mannitol, 150.0 g of crystalline cellulose and 50.0 g of croscarmellose sodium by the same method as described in Example 2-1. The desired aluminum bag packaged product was obtained by the same method as described in Example 2-2 from the tablet obtained.

Example 3-2

Preparation of a Tablet without the Addition of Crystalline Cellulose and an Aluminum Bag Packaged Product Thereof A tablet was prepared using 3.8 g of Compound A, 896.2 g of D-mannitol and 50.0 g of croscarmellose sodium by the same method as described in Example 2-1. The desired aluminum bag packaged product was obtained by the same method as described in Example 2-2 from the tablet obtained.

The compositions of each ingredient in the tablets obtained in Examples 2-1, 2-2, 3-1 and 3-2 are shown in the following Table 4.

TABLE 4

| Ingredient | Example 2-1 | Example 2-2 | Example 3-1 | Example 3-2 |
|---|---|---|---|---|
| Compound A (mg) | 0.5 | 0.5 | 0.5 | 0.5 |
| D-mannitol (mg) | 84.0 | 84.0 | 97.0 | 116.5 |
| Crystalline cellulose (mg) | 32.5 | 32.5 | 19.5 | — |
| Croscarmellose sodium (mg) | 6.5 | 6.5 | 6.5 | 6.5 |
| Hydroxypropyl-cellulose (mg) | 3.9 | 3.9 | 3.9 | 3.9 |
| Magnesium stearate (mg) | 2.6 | 2.6 | 2.6 | 2.6 |
| Coating mixture 1 (mg) | 6.5 | 6.5 | 6.5 | 6.5 |
| Total | 137 mg | 137 mg | 137 mg | 137 mg |

Test Example 2

The aluminum bag packaged product obtained in Examples 2-1 and 2-2 was stored under the conditions of 60° C. for one month and the production of related substances in the tablet under the same conditions as Test Example 1 was evaluated. The results are shown in Table 5. As for the tablets in the aluminum bag packaged products obtained in Examples 2-1 and 2-2, the production of individual related substances and the total production of the related substances were suppressed. Also, as for the tablet in the aluminum bag packaged product obtained in Example 2-1 (using aluminum foil in which the amount of melamine resin in an adhesive is reduced), the production of the related substances with relative retention time (RRT) of 1.28 and the total production of the related substances were remarkably suppressed as compared to those of Example 2-2.

TABLE 5

Production of related substances (RRT: Relative Retention Time, Storage condition: 60° C.)

| Sample | Storage period | Amount of related substances (%) | | | | |
|---|---|---|---|---|---|---|
| | | RRT0.45 | RRT0.52 | RRT0.99 | RRT1.28 | Total |
| Example 2-1 | At the onset | ND | 0.20 | <0.05 | ND | 0.38 |
| | One month | ND | 0.96 | 0.15 | 0.15 | 1.93 |
| Example 2-2 | At the onset | ND | 0.20 | <0.05 | ND | 0.38 |
| | One month | ND | 0.33 | 0.08 | 1.26 | 10.32 |

ND: Below the detection limit.

Test Example 3

The aluminum bag packaged products obtained in Examples 2-1, 3-1 and 3-2 were stored under the conditions of 60° C. for one month and the production of related substances in the tablet was evaluated under the measurement condition 2 described as follows. The results are shown in Table 6. As for the tablets in aluminum bag packaged products obtained in Examples 2-1, 3-1 and 3-2, the production of individual related substances and the total production of the related substances were suppressed. Also, as for the tablets of aluminum bag packaged products obtained in Examples 2-1 and 3-1, the production of the related substances was suppressed as compared to that obtained in Example 3-2. Furthermore, as for Example 2-1 in which the amount of the crystalline cellulose added was large, the suppressive effect of the production of related substances was remarkable.

TABLE 6

Production of related substances (RRT (Relative Retention Time): 0.99, Storage condition: 60° C.)

| Storage period | Example 2-1 | Example 3-1 | Example 3-2 |
|---|---|---|---|
| At the onset | ND | ND | ND |
| One month | ND | 0.14% | 1.56% |

ND: Below the detection limit.

(Measurement Condition 2)

Detector: Ultraviolet absorption photometer (Measurement wavelength: 220 nm)

Column: L-column2 (CERI) 4.6 mm I.D.×150 mm

Column temperature: constant temperature at approximately 40° C.

Mobile phase solution A: water/acetonitrile/trifluoroacetic acid (1900/100/1)

Mobile phase solution B: acetonitrile/water/trifluoroacetic acid (1800/200/1)

Flow rate: 1.0 mL/min

Method for feeding Mobile phase solutions: The solution was supplied at the ratio of Mobile phase solution A/Mobile phase solution B (79/21).

Example 4-1

Preparation of a Tablet with the Addition of Calcium Carbonate

In a fluidized-bed granulator (FLO-2, Freund Corporation), 7.69 g of Compound A, 1272.3 g of D-mannitol, 500.0 g of crystalline cellulose, 100.0 g of croscarmellose sodium and 20.0 g of calcium carbonate (Japanese Pharmacopoeia, Nitto Funka Kogyo K. K., the same shall apply hereinafter) were charged, the mixture was mixed and granulated by spraying 750.0 g of 8% by weight of hydroxypropylcellulose aqueous solution to obtain granulated granules after drying. The granulated granules obtained were cracked using a sizer (Comil QC197S, Powrex) to obtain uniformly sized granules. The uniformly sized granules obtained (980.0 g) and magnesium stearate (20.0 g) were mixed to obtain granules for tableting. The granules for tableting obtained were tableted using a tableting machine to obtain the desired tablet (mass: 130 mg, tablet shape: circular (7 mm in diameter)).

Example 4-2

Preparation of a Tablet without the Addition of Calcium Carbonate

In a fluidized-bed granulator (FLO-2, Freund Corporation), 7.69 g of Compound A, 1292.3 g of D-mannitol, 500.0 g of crystalline cellulose and 100.0 g of croscarmellose sodium were charged, the mixture was mixed and granulated by spraying 750.0 g of 8% by weight of hydroxypropylcellulose aqueous solution to obtain granulated granules after drying. The desired tablet (mass: 130 mg, tablet shape: circular (7 mm in diameter)) was obtained by the same method as described in Example 4-1 using the granulated granules obtained.

Example 5-1

Preparation of a Tablet with the Addition of Calcium Carbonate

In a fluidized-bed granulator (FLO-2, Freund Corporation), 7.69 g of Compound A, 1252.3 g of D-mannitol, 500.0 g of crystalline cellulose, 100.0 g of croscarmellose sodium and 40.0 g of calcium carbonate were charged, the mixture was mixed, and granulated by spraying 750.0 g of 8% by weight of hydroxypropylcellulose aqueous solution to obtain granulated granules after drying. The desired tablet (mass: 130 mg, tablet shape: circular (7 mm in diameter)) was obtained by the same method as described in Example 4-1 using the granulated granules obtained.

The compositions of each ingredient in the tablets obtained in Examples 4-1, 4-2 and 5-1 are shown in the following Table 7.

TABLE 7

| Ingredient | Example 4-1 | Example 4-2 | Example 5-1 |
|---|---|---|---|
| Compound A (mg) | 0.5 | 0.5 | 0.5 |
| D-mannitol (mg) | 82.7 | 84.0 | 81.4 |
| Crystalline cellulose (mg) | 32.5 | 32.5 | 32.5 |
| Croscarmellose sodium (mg) | 6.5 | 6.5 | 6.5 |
| Calcium carbonate (mg) | 1.3 | — | 2.6 |
| Hydroxypropylcellulose (mg) | 3.9 | 3.9 | 3.9 |
| Magnesium stearate (mg) | 2.6 | 2.6 | 2.6 |
| Total | 130 mg | 130 mg | 130 mg |

Test Example 4

Tablets obtained in Examples 4-1, 4-2 and 5-1 were placed in a glass bottle (open) and stored under the conditions of 40° C./75% RH for one month, and the amount of production of related substances was evaluated according to the measurement condition 1. The results are shown in Table 8. As for the tablets obtained in Examples 4-1, 4-2 and 5-1, the production of individual related substances and the total production of the related substances were suppressed. Also, as compared to the tablet obtained in Example 4-2, the production of related substances after storing (RRT (relative retention time) 0.52 and the total amount) of the tablets obtained in Examples 4-1 and 5-1 with the addition of calcium carbonate was more suppressed. Furthermore, the effect was remarkable in Example 5-1.

TABLE 8

Production of related substances (RRT: Relative Retention Time, Storage condition: 40° C./75% RH)

| Sample | Storage period | Amount of related substances (%) | |
|---|---|---|---|
| | | RRT0.52 | Total |
| Example 4-1 | At the onset | 0.28 | 0.41 |
| | One month | 1.32 | 1.62 |
| Example 4-2 | At the onset | 0.35 | 0.47 |
| | One month | 2.86 | 3.27 |
| Example 5-1 | At the onset | 0.25 | 0.37 |
| | One month | 0.88 | 1.16 |

ND: Below the detection limit.

Example 5-2

Preparation of a Tablet without Coating

The desired uncoated tablet (mass: 130 mg, tablet shape: circular (7 mm in diameter), the same shall apply hereinafter) was obtained by the same method as described in Example 1-2.

Example 6

Preparation of a Tablet with Coating

The above coating mixture 1 was dispersed in purified water to prepare a coating solution with a solid component concentration of 10% by weight. The desired tablet was obtained using a tablet coating machine (DRC-200, Powrex) by coating the uncoated tablet obtained in Example 5-2 with the coating film adjusted to 4 parts by weight in the dry state per 100 parts by weight of the uncoated tablet.

Example 7

Preparation of a Tablet with Coating

The above coating mixture 1 was dispersed in purified water to prepare a coating solution with a solid component concentration of 10% by weight. The desired tablet was obtained using a tablet coating machine (DRC-200, Powrex) by coating the uncoated tablet obtained in Example 5-2 with the coating film adjusted to 6 parts by weight in the dry state per 100 parts by weight of the uncoated tablet.

Example 8

Preparation of a Tablet with Coating

The above coating mixture 1 was dispersed in purified water to prepare a coating solution containing a solid component concentration of 10% by weight. The desired tablet was obtained using a tablet coating machine (DRC-200, Powrex) by coating the uncoated tablet obtained in Example 5-2 with the coating film adjusted to 8 parts by weight in the dry state per 100 parts by weight of the uncoated tablet.

The compositions of each ingredient in the tablet obtained in Examples 6 to 8 and Example 5-2 are shown in the following Table 9.

TABLE 9

| Ingredient | Example 6 | Example 7 | Example 8 | Example 5-2 |
|---|---|---|---|---|
| Compound A (mg) | 1.0 | 1.0 | 1.0 | 1.0 |
| Lactose hydrate (mg) | 104.3 | 104.3 | 104.3 | 104.3 |
| Low-substituted hydroxypropylcellulose (mg) | 19.5 | 19.5 | 19.5 | 19.5 |
| Hydroxypropylcellulose (mg) | 3.9 | 3.9 | 3.9 | 3.9 |
| Magnesium stearate (mg) | 1.3 | 1.3 | 1.3 | 1.3 |
| Coating mixture 1 (mg) | 5.2 | 7.8 | 10.4 | — |
| Total | 135 mg | 138 mg | 140 mg | 130 mg |

Test Example 5

According to a photostability test guideline on new drug substances and new preparations in the International Conference on Harmonization of Technical Requirements for Registration of Pharmaceuticals for Human Use (ICH) (Nov. 6, 1996), a photostability test of tablets obtained in Examples 6 to 8 and 5-2 was carried out under the following conditions. After light exposure, the production of the related substances (RRT (relative retention time) 0.52 and the total amount) was evaluated according to the measurement condition 1. The results are shown in Table 10. As for any tablets obtained in Examples 6 to 8 and 5-2, the production of individual related substances and the total production of related substances were suppressed. Also, the production of the related substances after light exposure (RRT (relative retention time) 0.52 and the total production) in tablets with coating in Examples 6 to 8 was more suppressed as compared to the tablet obtained in Example 5-2.

TABLE 10

Production of related substances (RRT: Relative Retention Time, Light-exposure conditions: total illuminance 120,000 lxh)

| Sample | Storage period | Amount of related substances (%) | |
| --- | --- | --- | --- |
| | | RRT0.52 | Total |
| Example 6 | Before light-exposure | 0.33 | 0.96 |
| | After light-exposure | 0.56 | 1.31 |
| Example 7 | Before light-exposure | 0.38 | 1.03 |
| | After light-exposure | 0.47 | 1.16 |
| Example 8 | Before light-exposure | 0.39 | 1.05 |
| | After light-exposure | 0.44 | 1.11 |
| Example 5-2 | Before light-exposure | 0.30 | 0.84 |
| | After light-exposure | 2.49 | 4.54 |

(Photostability Test Condition)
Light source: Xenon lamp
Illuminance: 30,000 lx
Exposure time: 40 hours (Total illuminance 120,000 lxh)

Example 9-1

Preparation of an Aluminum Bag Packaged Product in which a Deoxidizer and Desiccant are not Enclosed In a fluidized-bed granulator (FLO-15, Freund Corporation), 63.1 g of Compound A, 10432.9 g of D-mannitol, 4100.0 g of crystalline cellulose, 820.0 g of croscarmellose sodium and 492.0 g of calcium carbonate were charged, the mixture was mixed and granulated by spraying 6150.0 g of 8% by weight hydroxypropylcellulose aqueous solution to obtain granulated granules after drying. The granulated granules obtained were cracked using a sizer to obtain uniformly sized granules. The uniformly sized granules obtained (8000.0 g) and magnesium stearate (163.3 g) were mixed using a mixer (TBM-60, Tokuju Co., Ltd., the same shall apply hereinafter) to obtain granules for tableting. An uncoated tablet was obtained by tableting the granules obtained for tableting using a tableting machine (AQUARIUS, made by Kikusui Seisakusho, LTD.). A coating mixture 2 (52.0 g hypromellose (substitution degree type: 2910, viscosity: 3 mPa·s) (Japanese Pharmacopoeia), 20.0 g of titanium oxide (Japanese Pharmacopoeia), 14.0 g of Macrogol 6000 (Japanese Pharmacopoeia), 10.0 g of lactose hydrate (Japanese Pharmacopoeia), and 4.0 g of yellow ferric oxide (Japanese Pharmaceutical Excipients) are contained in 100 g of the coating mixture 2) were dispersed in purified water to prepare a coating solution with a solid component concentration of 10% by weight. A tablet was obtained using a tablet coating machine (DRC-500, Powrex) by coating 3500.0 g of the uncoated tablet with the coating film adjusted to 5 parts by weight in the dry state per 100 parts by weight of the uncoated tablet. After the tablet obtained was stored under the conditions of 25° C./60% RH for 5 days, a blister pack product was obtained by using a PTP packaging machine (No. 8 55PX type, Iwakuro Mfg. Co., Ltd.) using a polypropylene sheet (TAS-2230V, Taisei Chemical Industries, Ltd.) and aluminum foil (UACJ) in which the amount of melamine resin in adhesive agent was reduced. The blister pack product obtained was placed in an aluminum bag (HOSOKAWA YOKO Co., Ltd., the same shall apply hereinafter) and the aluminum bag was sealed using a heat sealer (Quick Sheeler, Shiga packaging machine, the same shall apply hereinafter) to obtain the desired aluminum bag packaged product.

Example 9-2

An Aluminum Bag Packaged Product with a Deoxidizer Enclosed

A blister pack product was obtained by the same method as described in Example 9-1. Ten sheets of blister pack product and a deoxidizer (PharmaKeep KC-20, Mitsubishi Gas Chemical Company Inc.) were placed in an aluminum bag (HOSOKAWA YOKO Co. Ltd., the same shall apply hereinafter) and the aluminum bag was sealed using a heat sealer to obtain the desired aluminum bag packaged product.

Example 10

Preparation of an Aluminum Bag Packaged Product with a Desiccant Enclosed

A blister pack product was obtained by the same method as described in Example 9-1. Ten sheets of a blister pack product and a desiccating agent (MS Serum W 3G, Tokai Chemical Industry Co., Ltd.) were placed in an aluminum bag (HOSOKAWA YOKO Co. Ltd.), and the aluminum bag was sealed using a heat sealer (Quick Sheeler, Shiga Hosoki, Co. Ltd., the same shall apply hereinafter) to obtain the desired aluminum bag packaged product.

The compositions of each ingredient in the tablets obtained in Examples 9-1, 9-2 and 10 are shown in the following Table 11.

TABLE 11

| Ingredient | Examples 9-1, 9-2 and 10 |
| --- | --- |
| Compound A (mg) | 0.5 |
| D-mannitol (mg) | 82.7 |
| Crystalline cellulose (mg) | 32.5 |
| Croscarmellose sodium (mg) | 6.5 |
| Calcium carbonate (mg) | 1.3 |
| Hydroxypropylcellulose (mg) | 3.9 |
| Magnesium stearate (mg) | 2.6 |
| Coating mixture 2 (mg) | 6.5 |
| Total | 137 mg |

Test Example 6

The aluminum bag packaged products obtained in Examples 9-1, 9-2 and 10 were stored under the conditions of 60° C. for one month and the production of related substances in the tablet was evaluated according to the same conditions as the Test Example 1. The results are shown in Table 12. As for the tablets obtained in Examples 9-1, 9-2 and 10, the production of individual related substances and the total production of the related substances were suppressed. In addition, after the storage, the total production of the related substances in the tablets in the aluminum bag packaged product obtained in Examples 9-2 and 10 was more suppressed compared with that in Example 9-1. The effect was remarkable, particularly in Example 9-2.

TABLE 12

Production of related substances (RRT: Relative Retention Time, Storage condition: 60° C.)

| Sample | Storage period | Amount of related substances (%) | |
|---|---|---|---|
| | | RRT0.52 | Total |
| Example 9-1 | At the onset | 0.25 | 0.25 |
| | One month | 0.92 | 1.58 |
| Example 9-2 | At the onset | 0.25 | 0.25 |
| | One month | 0.22 | 0.22 |
| Example 10 | At the onset | 0.25 | 0.25 |
| | One month | 0.27 | 0.53 |

Example 11-1

Preparation of a Tablet without Coating with a Polyvinyl Alcohol-Polyethylene Glycol Graft Copolymer In a fluidized-bed granulator (FLO-15, Freund Corporation), 38.5 g of Compound A, 6161.5 g of D-mannitol, 1250.0 g of crystalline cellulose, 250.0 g of croscarmellose sodium and 50.0 g of calcium carbonate were charged, the mixture was mixed and granulated by spraying 1875.0 g of 8% by weight of hydroxypropylcellulose aqueous solution to obtain granulated granules after drying. The granulated granules obtained were cracked using a sizer (Comil QC-197S, Powrex) to obtain uniformly sized granules. The uniformly sized granules obtained (4410.0 g) and magnesium stearate (90.0 g) were mixed using a mixer (TBM-25, Tokuju Co., Ltd.) to obtain granules for tableting. The granules for tableting obtained were tableted using a tableting machine (AQUARIUS, made by Kikusui Seisakusho, LTD.) to obtain an uncoated tablet. The coating mixture 2 was dispersed in purified water to prepare a coating solution with a solid component concentration of 10% by weight. A tablet was obtained by coating 3500.0 g of the uncoated tablet using a tablet coating machine (DRC-500, Powrex) with the coating film adjusted to 8 parts by weight in the dry state per 100 parts by weight of the uncoated tablet.

Example 11-2

Preparation of a Tablet Coated with a Polyvinyl Alcohol-Polyethylene Glycol Graft Copolymer An uncoated tablet was obtained by the same method as described in Example 11-1. A polyvinyl alcohol-polyethylene glycol graft copolymer (Kollicoat IR (registered trademark), BASF) was dissolved in purified water to prepare a coating solution 1 with a solid component concentration of 5% by weight. Furthermore, the coating mixture 2 was dispersed into purified water to prepare a coating solution 2 with a solid component concentration of 10% by weight. A tablet was obtained using a tablet coating machine (DRC-200, Powrex) by spraying the coating solution 1 and coating with the coating film adjusted to 2 parts by weight in the dry state per 100 parts by weight of the uncoated tablet, and subsequently spraying the coating solution 2 and coating with the coating film adjusted to 5 parts by weight in the dry state per 100 parts by weight of the uncoated tablet.

The compositions of each ingredient in the tablets obtained in Examples 11-1 and 11-2 are shown in the following Table 13.

TABLE 13

| Ingredient | Example 11-1 | Example 11-2 |
|---|---|---|
| Compound A (mg) | 1.0 | 1.0 |
| D-mannitol (mg) | 82.2 | 82.2 |
| Crystalline cellulose (mg) | 32.5 | 32.5 |
| Croscarmellose sodium (mg) | 6.5 | 6.5 |
| Calcium carbonate (mg) | 1.3 | 1.3 |
| Hydroxypropylcellulose (mg) | 3.9 | 3.9 |
| Magnesium stearate (mg) | 2.6 | 2.6 |
| Polyethylene glycol-polyvinyl alcohol graft copolymer(mg) | — | 2.6 |
| Coating mixture 2 (mg) | 10.4 | 6.5 |
| Total | 140 mg | 139 mg |

Test Example 7

The tablets obtained in Examples 11-1 and 11-2 were placed in a plastic petri dish (open) and stored under the conditions of 25° C./60% RH for two weeks and one month, subsequently the production of related substances was evaluated according to the measurement condition 1. The results are shown in Table 14. As for any tablets obtained in Examples 11-1 and 11-2, the production of individual related substances and the total production of related substances were suppressed. Also, as for the tablet in Example 11-2, the production of the related substances after storing (RRT (relative retention time) 0.52 and the total amount) was more suppressed compared with those of the tablet obtained in Example 11-1.

TABLE 14

Production of related substances (RRT: Relative Retention Time, Storage condition: 25° C./60% RH)

| Sample | Storage period | Amount of related substances (%) RRT0.52 |
|---|---|---|
| Example 11-1 | At the onset | 0.14 |
| | Two weeks | 0.25 |
| | One month | 0.34 |
| Example 11-2 | At the onset | 0.14 |
| | Two weeks | 0.16 |
| | One month | 0.18 |

Example 12-1

Preparation of a Tablet without Containing a Basic Additive

In a fluidized-bed granulator (FLO-5, Freund Corporation), 22.5 g of Compound A, 3780.0 g of D-mannitol, 1462.5 g of crystalline cellulose and 292.5 g of croscarmellose sodium were charged, the mixture was mixed, and subsequently subjected to the same method as described in Example 1-1 to obtain a coated tablet.

Example 12-2

Preparation of a Tablet with the Addition of Calcium Silicate

In a fluidized-bed granulator (MP-01, Powrex), 3.8 g of Compound A, 646.2 g of D-mannitol, 250.0 g of crystalline cellulose and 50.0 g of croscarmellose sodium were charged, the mixture was mixed and granulated by spraying 375.0 g of a HPC-L aqueous solution to obtain granulated granules after drying. The granulated granules obtained were sieved using a sizer (Comil QC-197S, Powrex) to obtain uniformly sized granules. The uniformly sized granules obtained (388.1 g), calcium silicate (4.0 g, Nacalai Tesque, the same shall apply hereinafter) and magnesium stearate (7.9 g) were mixed to obtain granules for tableting. The granules for tableting obtained were tableted using a tableting machine (Correct 12, made by Kikusui Seisakusho, LTD.) to obtain the desired tablet (mass: 131 mg, tablet shape: circular (7 mm in diameter)).

Example 12-3

Preparation of a Tablet with the Addition of Calcium Silicate

The uniformly sized granules (380.3 g) obtained in Example 12-2, calcium silicate (11.9 g) and magnesium stearate (7.8 g) were mixed to obtain granules for tableting. The granules for tableting obtained were tableted using a tableting machine (Correct 12, made by Kikusui Seisakusho, LTD.) to obtain the desired tablet (mass: 134 mg, tablet shape: circular (7 mm in diameter)).

Example 12-4

Preparation of a Tablet with the Addition of Magnesium Aluminometasilicate

In a fluidized-bed granulator (MP-01, Powrex), 5.0 g of Compound A, 840.0 g of D-mannitol, 325.0 g of crystalline cellulose and 65.0 g of croscarmellose sodium were charged, the mixture was mixed and granulated by spraying 487.5 g of a HPC-L aqueous solution to obtain granulated granules after drying. The granulated granules obtained were sieved using a sizer (Comil QC-197S, Powrex) to obtain uniformly sized granules. The uniformly sized granules obtained (384.3 g), magnesium aluminometasilicate (7.8 g, Neusilin FH2 (registered trademark), Fuji Chemical Industries, Co., Ltd.) and magnesium stearate (7.8 g) were mixed to obtain granules for tableting. The granules for tableting obtained were tableted using a tableting machine (Correct 12, made by Kikusui Seisakusho, LTD.) to obtain the desired tablet (mass: 133 mg, tablet shape: circular (7 mm in diameter)).

The compositions of each ingredient in the tablets obtained in Examples 12-1, 12-2, 12-3 and 12-4 are shown in the following Table 15.

TABLE 15

| Ingredient | Example 12-1 | Example 12-2 | Example 12-3 | Example 12-4 |
|---|---|---|---|---|
| Compound A (mg) | 0.5 | 0.5 | 0.5 | 0.5 |
| D-mannitol (mg) | 84.0 | 84.0 | 84.0 | 84.0 |
| Crystalline cellulose (mg) | 32.5 | 32.5 | 32.5 | 32.5 |
| Croscarmellose sodium (mg) | 6.5 | 6.5 | 6.5 | 6.5 |
| Hydroxypropyl-cellulose (mg) | 3.9 | 3.9 | 3.9 | 3.9 |
| Magnesium stearate (mg) | 2.6 | 2.6 | 2.6 | 2.6 |
| Calcium silicate (mg) | — | 1.3 | 4.0 | — |
| Magnesium aluminometasilicate (mg) | — | — | — | 2.6 |
| Coating mixture 1 (mg) | 6.5 | — | — | — |
| Total | 136.5 mg | 131.3 mg | 134 mg | 132.6 mg |

Test Example 8

The tablets obtained in Examples 12-1, 12-2, 12-3 and 12-4 were placed in a brown glass bottle (open) and stored under the conditions of 40° C./75% RH for one month, and the production of related substances was evaluated according to the measurement condition 1. The results are shown in Table 16. As for any tablets obtained in Examples 12-1, 12-2, 12-3 and 12-4, the production of individual related substances and the total production of the related substances were suppressed. Also, as for the tablet obtained in Examples 12-2, 12-3 and 12-4, the production of the related substances after storing (RRT (relative retention time) 0.52 and the total amount) was more suppressed compared with the tablet obtained in Example 12-1.

TABLE 16

Production of related substances (RRT: Relative Retention Time), (Storage condition: 40° C./75% RH)

| | | Amount of related substances (%) | | | | | |
|---|---|---|---|---|---|---|---|
| Sample | Storage period | RRT approx. 0.52 | RRT approx. 0.99 | RRT approx. 1.03 | RRT approx. 1.06 | RRT approx. 1.10 | Total |
| Example 12-1 | At the onset | 0.29 | NQ | 0.06 | NQ | 0.07 | 0.42 |
| | One month | 1.94 | 0.11 | 0.05 | 0.08 | 0.06 | 2.24 |
| Example 12-2 | At the onset | 0.49 | NQ | 0.05 | 0.05 | 0.06 | 0.65 |
| | One month | 1.37 | 0.10 | 0.05 | 0.06 | 0.06 | 1.70 |
| Example 12-3 | At the onset | 0.51 | NQ | 0.06 | 0.05 | 0.07 | 0.69 |
| | One month | 1.43 | 0.10 | 0.05 | 0.07 | 0.06 | 1.77 |
| Example 12-4 | At the onset | 0.35 | 0.05 | 0.06 | NQ | 0.07 | 0.58 |
| | One month | 1.83 | 0.11 | 0.05 | 0.09 | 0.06 | 2.19 |

NQ: Not quantified

Example 13-1 Production of a Tablet Containing Croscarmellose Sodium as a Disintegrant In a fluidized-bed granulator (FLO-2, Freund Corporation), 7.69 g of Compound A, 1252.3 g of D-mannitol, 500.0 g of crystalline cellulose, 100.0 g of croscarmellose sodium and 40.0 g of calcium carbonate were charged, the mixture was mixed and subsequently subjected to the same method as described in Example 4-1 to obtain granules for tableting. The desired tablet (mass: 130 mg, tablet shape: circular (7 mm in a diameter)) was obtained by tableting using a tablet machine the granules for tableting obtained.

Example 13-2

Production of a Tablet Containing Low-Substituted Hydroxypropylcellulose as a Disintegrant In a fluidized-bed granulator (FLO-2, Freund Corporation), 7.69 g of Compound A, 1152.3 g of D-mannitol, 500.0 g of crystalline cellulose, 200.0 g of low-substituted hydroxypropylcellulose and 40.0 g of calcium carbonate were charged, the mixture was mixed, and subsequently subjected to the same method as described in Example 13-1 to obtain the tablet (mass: 130 mg, tablet shape: circular (7 mm in a diameter)).

The compositions of each ingredient in the tablets obtained in Example 13-1 and Example 13-2 are shown in the following Table 17.

TABLE 17

| Ingredient | Example 13-1 | Example 13-2 |
|---|---|---|
| Compound A (mg) | 0.5 | 0.5 |
| D-mannitol (mg) | 81.4 | 74.9 |
| Crystalline cellulose (mg) | 32.5 | 32.5 |
| Croscarmellose sodium (mg) | 6.5 | — |
| Calcium carbonate (mg) | 2.6 | 2.6 |
| Low-substituted hydroxypropylcellulose (mg) | — | 13.0 |
| Hydroxypropylcellulose (mg) | 3.9 | 3.9 |
| Magnesium stearate (mg) | 2.6 | 2.6 |
| Total | 130 mg | 130 mg |

Test Example 9

The tablets obtained in Examples 13-1 and 13-2 were placed in a brown glass bottle (open) and stored under the conditions of 40° C./75% RH for one month, and the production of related substances was evaluated according to the measurement condition 1. The results are shown in Table 18. As for any tablets obtained in Examples 13-1 and 13-2, the production of individual related substances and the total production of the related substances were suppressed. Also, as for the tablet obtained in Example 13-2, the production of the related substances after storing (RRT (relative retention time) 0.52 and the total amount) was more suppressed compared with those of the tablet obtained in Example 13-1.

TABLE 18

Production of related substances (RRT: Relative Retention Time), (Storage condition: 40° C./75% RH)

| Sample | Storage period | Amount of related substances (%) | | | | | |
|---|---|---|---|---|---|---|---|
| | | RRT approx. 0.52 | RRT approx. 0.99 | RRT approx. 1.03 | RRT approx. 1.06 | RRT approx. 1.10 | Total |
| Example 13-1 | At the onset | 0.25 | NQ | 0.05 | NQ | 0.07 | 0.37 |
| | One month | 0.87 | 0.06 | 0.06 | 0.06 | 0.07 | 1.12 |
| Example 13-2 | At the onset | 0.25 | NQ | 0.05 | NQ | NQ | 0.35 |
| | One month | 0.55 | 0.05 | 0.06 | 0.06 | 0.07 | 0.85 |

NQ: Not quantified

The invention claimed is:

1. A pharmaceutical composition, comprising:
   (4-{(3S)-3-[(1R)-1-(naphthalen-1-yl)ethylamino]pyrrolidin-1-yl}phenyl)acetic acid (Compound A) or a pharmacologically acceptable salt thereof;
   at least one diluent selected from the group consisting of a sugar, a sugar alcohol, a cellulose derivative, a starch derivative, and an inorganic salt; and
   at least one basic additive selected from the group consisting of calcium carbonate, calcium silicate, and magnesium aluminometasilicate.

2. The pharmaceutical composition of claim 1, wherein the diluent is at least one selected from the group consisting of lactose, white sugar, maltose, sucrose, mannitol, sorbitol, erythritol, maltitol, xylitol, glucose, crystalline cellulose, corn starch, potato starch, calcium monohydrogen phosphate, calcium dihydrogen phosphate, sodium dihydrogen phosphate and calcium phosphate.

3. The pharmaceutical composition of claim 1, wherein the diluent is contained in an amount of from 0.1 parts by weight to 99.9 parts by weight per 100 parts by weight of the pharmaceutical composition.

4. The pharmaceutical composition of claim 1, further comprising:
   at least one additive selected from the group consisting of a binder, a disintegrant, a lubricant, a coloring agent and a polishing agent.

5. The pharmaceutical composition of claim 4, wherein the binder is at least one selected from the group consisting of hydroxypropylcellulose, hydroxypropylmethylcellulose, methylcellulose, carboxymethylcellulose, carboxymethylethylcellulose, hydroxypropyl starch, hydroxyethylcellulose, hydroxypropylmethylcellulose acetate succinate, hydroxypropylmethylcellulose phthalate, carboxyvinyl polymer, polyvinylpyrrolidone, polyvinyl alcohol, methacrylate copolymer, macrogol, starch, gelatin, dextrin, pullulan, agar and gum Arabic.

6. The pharmaceutical composition of claim 4, wherein the disintegrant is at least one selected from the group consisting of croscarmellose sodium, crospovidone, sodium carboxymethyl starch, low-substituted hydroxypropylcellulose, carboxymethylcellulose, carboxymethylcellulose calcium, partially pregelatinized starch and starch.

7. The pharmaceutical composition of claim 4, wherein the lubricant is at least one selected from the group consisting of magnesium stearate, calcium stearate, talc, glyceryl monostearate, light anhydrous silicic acid, sodium stearyl fumarate and sucrose fatty acid esters.

8. The pharmaceutical composition of claim 4, wherein the coloring agent is at least one selected from the group consisting of yellow ferric oxide, titanium oxide, talc, ferric oxide, black iron oxide, copper chlorophyll, sodium copper chlorophylline, carbon black, medicinal charcoal, food dye, licorice extract, green tea powder, riboflavin, riboflavin butyrate, riboflavin sodium phosphate, and octyldodecyl myristate.

9. The pharmaceutical composition of claim 4, wherein the polishing agent is at least one selected from the group consisting of carnauba wax, shellac, beeswax, hardened oil and magnesium stearate.

10. The pharmaceutical composition of claim 4, wherein the additive is contained in an amount of from 0.1 parts by weight to 99.9 parts by weight per 100 parts by weight of the pharmaceutical composition.

11. The pharmaceutical composition of claim 1, wherein the pharmaceutical composition has a coating film.

12. The pharmaceutical composition of claim 11, wherein the coating film comprises at least one coating agent selected from the group consisting of a water-soluble polymer, lactose, white sugar, titanium oxide and talc.

13. The pharmaceutical composition of claim 12, wherein the water-soluble polymer is at least one selected from the group consisting of polyvinyl alcohol-polyethylene glycol graft copolymer, polyvinylpyrrolidone, hypromellose, hydroxypropylcellulose, polyvinyl alcohol, polyvinyl alcohol-acrylic acid-methyl methacrylate copolymer and polyethylene glycol.

14. The pharmaceutical composition of claim 12, wherein the coating agent is contained in an amount of from 0.1 parts by weight to 100 parts by weight per 100 parts by weight of the coating film.

15. The pharmaceutical composition of claim 11, wherein the coating film comprises a first coating film comprising a polyvinyl alcohol-polyethylene glycol graft copolymer and a second coating film comprising at least one agent selected from the group consisting of a water-soluble polymer, lactose, white sugar, titanium oxide and talc.

16. The pharmaceutical composition of claim 15, wherein the second coating film comprises at least one agent selected from the group consisting of a water-soluble polymer, lactose and titanium oxide.

17. The pharmaceutical composition of claim 16, wherein the second coating film further comprises a coloring agent.

18. The pharmaceutical composition of claim 4,
wherein the pharmaceutical composition has a coating film comprising at least one coating agent selected from the group consisting of a water-soluble polymer, lactose, white sugar, titanium oxide and talc, and
the pharmaceutical composition comprises:
from 0.5 to 5.0 parts by weight of the Compound A or a pharmacologically acceptable salt thereof,
from 50.0 to 90.0 parts by weight of the diluent,
from 1.0 to 5.0 parts by weight of the binder,
from 0.5 to 5.0 parts by weight of the basic additive,
from 2.0 to 10.0 parts by weight of the disintegrant,
from 0.5 to 3.0 parts by weight of the lubricant,
from 3.0 to 10.0 parts by weight of the coating agent, and
from 0.1 to 1.0 parts by weight of the coloring agent,
per 100 parts by weight of the pharmaceutical composition.

19. The pharmaceutical composition of claim 1, which comprises:
from 0.5 to 5.0 parts by weight of the Compound A or a pharmacologically acceptable salt thereof,
from 50.0 to 90.0 parts by weight of the diluent, and
from 0.5 to 5.0 parts by weight of the basic additive,
per 100 parts by weight of the pharmaceutical composition.

20. The pharmaceutical composition of claim 1, which comprises:
from 0.5 to 5.0 parts by weight of the Compound A or a pharmacologically acceptable salt thereof,
from 85 to 90 parts by weight of the diluent, and
from 0.99 to 3.0 parts by weight of the basic additive,
per 100 parts by weight of the pharmaceutical composition.

* * * * *